US008926610B2

(12) United States Patent
Hafner et al.

(10) Patent No.: US 8,926,610 B2
(45) Date of Patent: Jan. 6, 2015

(54) ELECTROSURGICAL INSTRUMENT

(75) Inventors: Dieter Hafner, Breisgau (DE); Florian Eisele, Breisgau (DE)

(73) Assignee: ERBE Elektromedizin GmbH, Tuebingen (DE)

( * ) Notice: Subject to any disclaimer, the term of this patent is extended or adjusted under 35 U.S.C. 154(b) by 1482 days.

(21) Appl. No.: 12/089,369

(22) PCT Filed: Sep. 26, 2006

(86) PCT No.: PCT/EP2006/009325
§ 371 (c)(1),
(2), (4) Date: Apr. 4, 2008

(87) PCT Pub. No.: WO2007/039185
PCT Pub. Date: Apr. 12, 2007

(65) Prior Publication Data
US 2008/0215048 A1    Sep. 4, 2008

(30) Foreign Application Priority Data

Oct. 4, 2005 (DE) .......... 10 2005 047 405
Sep. 13, 2006 (DE) .......... 10 2006 042 985

(51) Int. Cl.
| A61B 18/14 | (2006.01) |
| A61B 17/29 | (2006.01) |
| A61B 17/28 | (2006.01) |
| A61B 19/00 | (2006.01) |
| A61B 18/00 | (2006.01) |

(52) U.S. Cl.
CPC ......... *A61B 18/1442* (2013.01); *A61B 17/2909* (2013.01); *A61B 2019/304* (2013.01); *A61B 2018/00589* (2013.01); *A61B 2018/00601* (2013.01); *A61B 17/2841* (2013.01); *A61B 18/1445* (2013.01)
USPC .............................. 606/52; 606/51

(58) Field of Classification Search
CPC ................. A61B 18/1442; A61B 2018/00595; A61B 2018/00601; A61B 2018/1462; A61B 2019/304
USPC ...................................... 606/50–52
See application file for complete search history.

(56) References Cited

U.S. PATENT DOCUMENTS 3,911,241 A    10/1975 Jarrard
4,076,028 A *  2/1978 Simmons ............. 606/51
(Continued)

FOREIGN PATENT DOCUMENTS

| DE | 1 901 084   | 9/1964 |
| DE | 1 901 084 U | 9/1964 |

(Continued)

*Primary Examiner* — Michael Peffley
*Assistant Examiner* — Samantha Good
(74) *Attorney, Agent, or Firm* — Dickstein Shapiro LLP

(57) ABSTRACT

An electrosurgical instrument for coagulating and/or cutting biological tissue which can be manufactured easily and economically and which allows a surgical intervention to be carried out easily and reliably The instrument includes two linked branches which can be moved toward one another, gripping devices at a proximal region of the branches or of the instrument for bringing the branches together, electrode parts at a distal region of the branches or of the instrument for grasping tissue and for conducting a high-frequency current through the tissue, current feed devices for feeding the high-frequency current to the electrode parts from a high-frequency generator, a switching device for activating the high-frequency current with the branches brought together, at least one spacing element to form a defined minimum spacing between the electrode parts, and at least one elastically deformable element, which is arranged at one of the branches or the gripping devices such that, on closing the branches and reaching the minimum spacing, at least one region of the gripping devices can be moved further in the proximal region for actuating the switching device. The instrument can also be carried out as a shaft instrument, wherein at least one electrode part is movable through a shaft in its extension direction.

10 Claims, 6 Drawing Sheets

(56) References Cited

U.S. PATENT DOCUMENTS

| | | | |
|---|---|---|---|
| 4,274,413 A | 6/1981 | Hahn et al. | |
| 4,311,145 A | 1/1982 | Esty et al. | |
| 4,492,231 A | 1/1985 | Auth | |
| 4,552,143 A * | 11/1985 | Lottick | 606/42 |
| 5,122,139 A * | 6/1992 | Sutter | 606/51 |
| 6,110,171 A * | 8/2000 | Rydell | 606/51 |
| 6,270,497 B1 | 8/2001 | Sckino et al. | |
| 2001/0037110 A1 * | 11/2001 | Schmaltz et al. | 606/50 |
| 2003/0181910 A1 * | 9/2003 | Dycus et al. | 606/51 |
| 2004/0143263 A1 | 7/2004 | Schechter et al. | |

FOREIGN PATENT DOCUMENTS

| | | |
|---|---|---|
| DE | 41 13 075 C1 | 7/1992 |
| GB | 2 156 222 | 10/1985 |

* cited by examiner

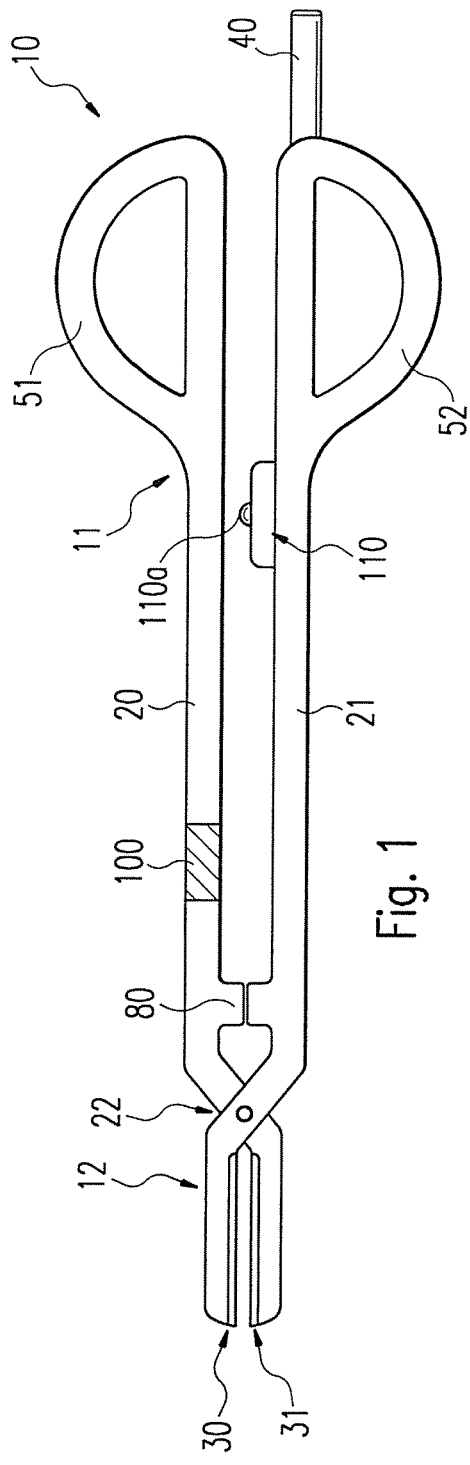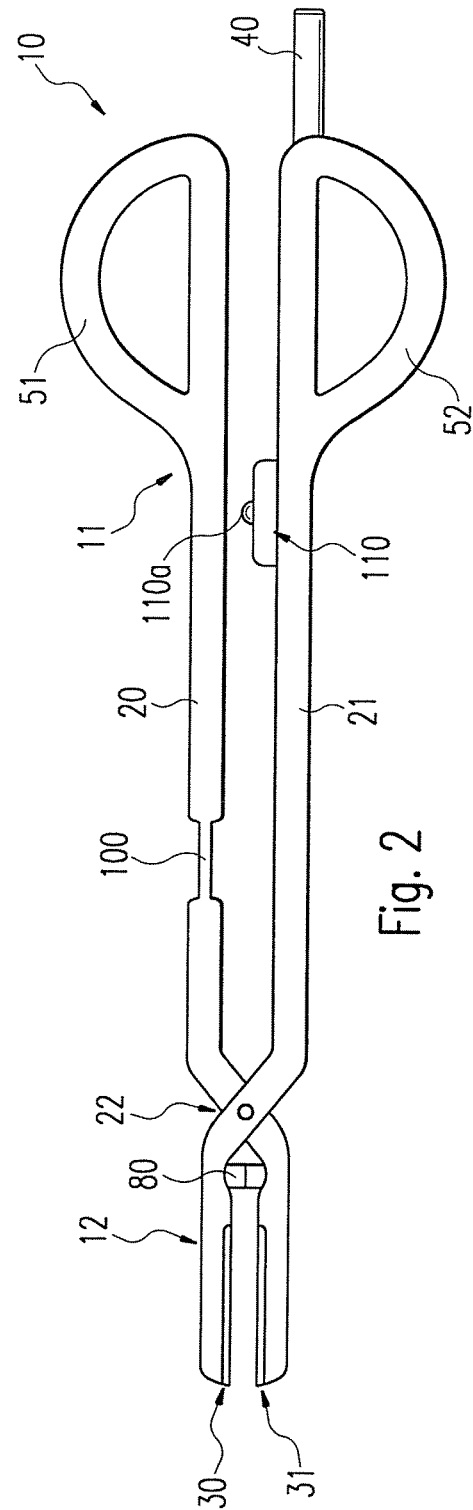

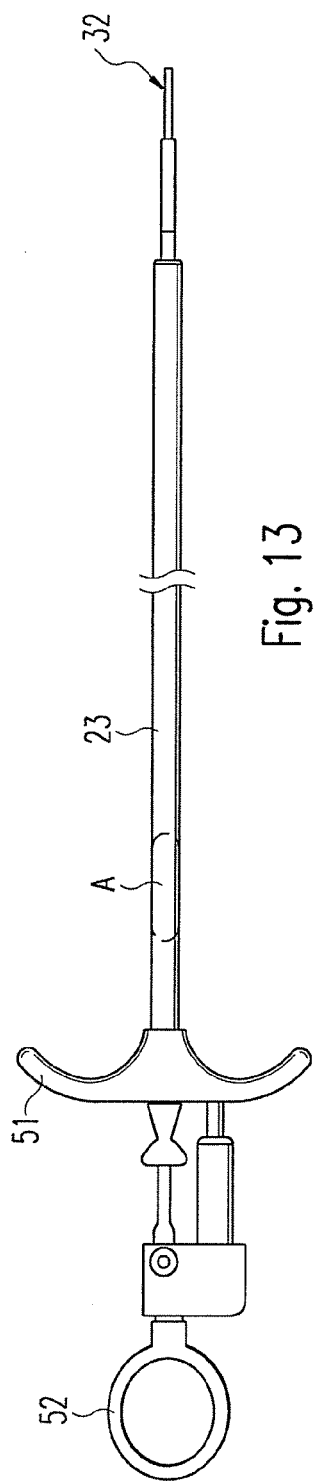
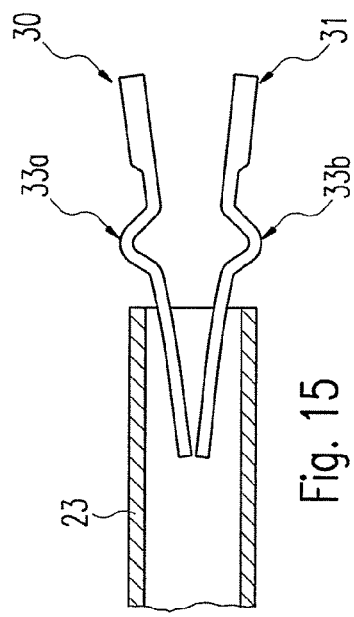
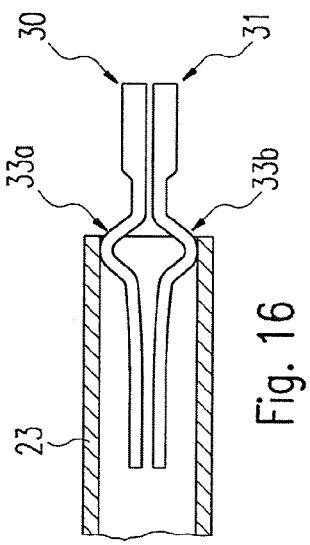
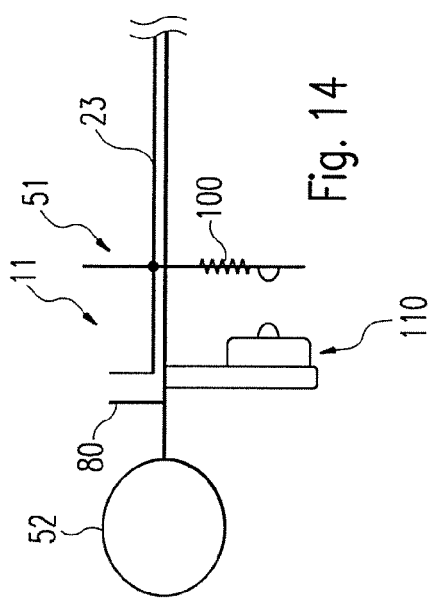
Fig. 13
Fig. 14
Fig. 15
Fig. 16

ELECTROSURGICAL INSTRUMENT

CROSS-REFERENCE TO RELATED APPLICATIONS

This application is the U.S. national stage of International Application No. PCT/EP2006/009325, filed Sep. 26, 2006, which claims priority to German applications DE 10 2005 047 405.5, filed Oct. 4, 2005, and DE 10 2006 042 985.0, filed Sep. 13, 2006.

FIELD OF THE INVENTION

The invention relates to an electrosurgical instrument, and more specifically, to an electrosurgical instrument used to coagulate or cut biological tissue.

BACKGROUND OF THE INVENTION

Electrosurgical instruments have been used for many years in the field of high frequency surgery to coagulate or cut biological tissue. For coagulation, a high frequency current is passed through the tissue being treated so that it changes, due to protein clotting and dehydration. The tissue contracts so that the vessels are closed and thus, bleeding is stopped. Following coagulation, the tissue can be completely separated without bleeding, either using a high frequency current or by mechanical means.

Electrosurgical processes can be carried out using unipolar or bipolar techniques. With the unipolar technique, the current path usually leads from the electrosurgical instrument via the tissue being treated to a neutral electrode and from there back to a high-frequency (HF) generator. However, bipolar instruments are increasingly gaining importance. These are constructed having two sections that are electrically insulated from one another. The current path between the electrode parts can be calculated and does not run long distances through the body of the patient. This reduces the effects, for example, on cardiac pacemakers and other devices that are attached to the patient during the operation.

Bipolar instruments usually have two branches joined in an articulated manner to one another. At their proximal end, gripping devices are provided for manipulating the branches. At the distal ends of the branches, electrode parts are provided for grasping tissue and conducting the high frequency current through the tissue. The current supplied by an HF generator is conducted via current supply lines to the electrode parts of the bipolar instrument.

Laparoscopic instruments are similarly constructed. They are tubular shafted instruments wherein the movement of the branches is transmitted via a deflecting mechanism, arranged in the interior of the tubular shaft, to the electrode parts arranged at the distal end of the tubular shaft. The branches are extended by means of the deflecting mechanism such that the electrode parts can be introduced via the tubular shaft into body cavities (e.g. the abdominal cavity) and actuated from "outside." This means that the proximal ends of the branches or the proximal region of the branches are transferred via the deflecting mechanism to the distal ends or the distal region of the branches with the electrode parts.

Unipolar instruments can be used for open surgery as well as for minimally invasive interventions (usually endoscopy).

In order to achieve reliable thermofusion of biological tissues, a variety of conditions must be observed. It must be possible to hold the tissue, for example, a blood vessel, reliably between the electrode parts to prevent it from slipping away. It is therefore required that a certain pressure is exerted on the tissue via the electrode parts. Furthermore, it must also be ensured that the electrode parts cannot be brought closer together than a minimum spacing, in order to avoid an unwanted short-circuit between the electrode parts.

In order to be able to perform a coagulation or a cutting procedure, the known instruments are connected to switches, for example, hand or foot switches. With these, the high frequency current which is fed to the tissue being treated can be activated.

With the aforementioned instruments, coagulation and/or cutting operations can be triggered at unfavourable time points by unintended actuation of the switches. The branches are often not completely closed and the tissue is not properly held between the branches, although current is already being fed to the tissue. This results, for example, in incomplete thermofusion, which can lead to dangerous after-bleeding or coagulation at unwanted sites. With unipolar instruments, current supply at an unfavourable time point can also bring about damage to the tissue being treated.

Furthermore, hand or foot switches require additional space and cause the instrument and the whole operation area to become more cluttered.

It is therefore an object of the invention to provide an electrosurgical instrument of the aforementioned type such that it can be produced easily and economically, and such that a surgical intervention can be easily and reliably performed with the instrument.

SUMMARY

In particular, the objectives of the invention may be achieved with an electrosurgical instrument for coagulating and/or cutting biological tissue, which may include: two linked branches which can be moved toward one another, gripping devices at a proximal region of the branches (or of the instrument) for bringing the branches together, electrode parts at a distal region of the branches (or of the instrument) for grasping tissue and for conducting a high-frequency current through the tissue, current feed devices for feeding the high-frequency current to the electrode parts from a high-frequency generator, a switching device for activating the high-frequency current with the branches brought together, at least one spacing element to form a defined minimum spacing between the electrode parts, and at least one elastically deformable element, which is arranged at one of the branches or the gripping devices such that, on closing the branches and reaching the minimum spacing, at least one region of the gripping devices can be moved further in the proximal region for actuating the switching device.

The spacing element, the elastically deformable element and the switching device are designed and arranged relative to one another such that the branch or gripping device lying opposed to the switching device can be brought into contact with the switching device for its activation. During their bringing together, the at least one region of the gripping devices in the proximal region passes through various "travel regions." Passage through a first travel region serves to move the electrode parts for grasping and holding the tissue, wherein a particular minimum spacing between the electrode parts cannot be passed due to the spacing element provided on the instrument. By this means, a short circuit between the electrode parts is avoided. As soon as the gripping device or the branches are brought together such that the minimum spacing is reached and the tissue being treated is securely held, at least one region of the gripping devices in the proximal region and possibly also at least one branch can be moved further, due to the elastically deformable element, such that actuation of the switching device, which is also arranged in the proximal region at this or the opposing branch or gripping device, is enabled. At least the gripping device or branch which can be moved further moves through a second "travel region" in order to bring the switching device and the opposing branch—as described above—into contact with one another. This means that the branches or gripping devices can be moved closer together in their proximal region, even if no further movement of the electrode parts is provided here. It is important that the elastically deformable element is integrated into the force transmitting path and therefore both the travel regions can be passed through. The current feed from the HF generator to the electrode parts can be activated via the switching device. For this purpose, the current feed devices have at least one current connection element on the instrument and, for example, lines which run through the instrument as far as the electrode parts in order to ensure current feed into the tissue via the electrode parts. The bringing together of the branches or gripping devices transfers the electrode parts, in principle, from a rest position (jaws open) to a working position (jaws substantially closed) to grasp the tissue.

Using this arrangement allows complex hand or foot switches for activating the HF current to be dispensed with, so that the operation area overall remains less cluttered. The instrument is easy to operate because a user only needs to bring the gripping devices together until complete closing of the branches in order to initiate the current supply (via the switching device) once the tissue is held. Thus the start of a coagulation and/or cutting process can be precisely adjusted in conjunction with the positioning of the tissue being treated. Deactivation of the HF current or interruption of the current supply can take place, for example, when the switching device is "released" again. Thus the current feed is maintained only for as long as the switching device is "pressed," (e.g., actuated) and a defined forced is transmitted via the gripping devices. It is also possible for the current feed to be deactivated by renewed actuation of the switching device or possibly through additional switching devices.

Preferably, the jaw part and thus the electrode parts, can only remain closed for grasping the tissue in principle for as long as force is applied via the gripping devices on the electrode parts. This is advantageous, above all, for rapid work. The electrode parts may possibly be forced back to their open position by a return mechanism, for example, a spring, whenever the gripping devices are not actuated. It is also possible that a latching mechanism fixes the closed electrode parts or the instrument is designed such that the electrode part(s) remain(s) in the desired position without additional devices.

The activation of the high frequency current just described can preferably be provided in electrosurgical instruments which are designed, for example, as scissor-type instruments for open surgery. Instruments for endoscopy, for example laparoscopic instruments, can also be constructed as described above without difficulty, making them easy and reliable to use. Laparoscopic instruments also have branches—just like, for example, bipolar scissors—which can be actuated in scissor-like manner and can be moved via the electrode parts. In practice, the branches in the proximal region are usually configured such that only one branch is movable whilst the other branch is, for example, configured integral with a housing and therefore fixed. In order to actuate the branches and thus the electrode parts, gripping devices are provided at a proximal region of the branches, whereas the electrode parts are formed at a distal region for grasping tissue and for conducting high frequency current through the tissue. In order to be able to carry out minimally invasive interventions, the branches are extended via a deflecting mechanism such that the movement of the branches can be transmitted via the gripping devices through the deflecting mechanism to the electrode parts. The deflecting mechanism is, for example, arranged within a tubular shaft which is formed between the proximal region and the distal region of the branches. The tubular shaft makes it possible to introduce the electrode parts into a body cavity, for example, into the abdominal cavity, wherein actuation of the electrode parts can be carried out from "outside" via the branches in the proximal region by means of the gripping devices. In laparoscopic instruments of this type, the spacing element, the elastically deformable element and the switching device are also arranged as in a scissor-type instrument for open surgery.

In a first preferred embodiment, the elastically deformable element is arranged between the switching device and the spacing element in the proximal region of the branches, so that the further movement of the respective gripping device for actuating the switching device can be carried out without difficulty. The spacing element can be arranged either in the proximal region of the branches or in the distal region, that is close to the electrode parts, or even on them.

However, the spacing element must be configured such that the desired minimum spacing between the electrode parts is defined, wherein on reaching the minimum spacing, further movement of the gripping device in the proximal region must be possible without the position of the electrode parts being altered.

In a further preferred embodiment, the elastically deformable element is arranged at the branch or at at least one of the gripping devices and interposed within it, and is configured such that a predefined bending or folding site is provided by the elastically deformable element on the branch or gripping device. The predefined bending or folding site permits bending or folding of at least the relevant gripping device or also at least one branch at the desired site without loading the remaining regions excessively, for example, by bending. Therefore, the at least one region of the gripping device can be further moved by simple means to actuate the switching device.

A preferred embodiment provides that the elastically deformable element is provided as a branch section or a gripping device section which is configured narrowed compared with the surrounding branch regions or gripping devices. By this means, without great effort, the predetermined bending or folding site can be carried out on at least one branch or at least one of the gripping devices and the desired bending or folding can be carried out without difficulty. Since branches and the elastically deformable element can be configured to be integrated with one another, the instrument can be manufactured easily and can be easily cleaned after an operation.

Fundamentally, both branches or gripping devices or, alternatively, only one of the branches or gripping devices can be configured with an elastically deformable element, specifically the branch or gripping device which has the switching device or the branch or gripping device opposed thereto. In any event, the gripping devices (and possibly also the branches) are moved toward one another for actuating the switching device, on account of the elastically deformable element. Apart from bending elements, extensible or stretchable elements or similar devices can also be provided. The elastically deformable element should always be integrated in the force transmitting path such that both "travel regions" can be passed through by the at least one gripping device.

One solution according to the invention provides that the spacing element is designed as a limit element at at least one branch. The limit element is arranged as a projection at one or both of the branches, so that bringing together the branches beyond the minimum spacing is prevented. Thus, a short-circuit between the electrode parts is avoided by the simplest means while, at the same time, the first "travel region" is defined by the spacing element so that the further movement of the corresponding gripping device is ensured even on reaching the minimum spacing between the electrode parts via the second "travel region."

In one embodiment, the switching device and the opposing branch or gripping device are configured such that the switching device can be actuated by contact with the opposing branch or gripping device. This means therefore that the switching device is actuated by merely contacting the opposing branch or gripping device. This is a particularly simple and economical arrangement for activating the high frequency current.

An actuating element, for example, an actuating peg provided at the branch or gripping device opposing the switching device may be arranged such that it actuates the switching device on further movement of the at least one region of the gripping devices, for example, by bending or folding at least one branch or gripping device. This is advantageous particularly when the switching device is arranged, for example, within the opposing branch or gripping device for protection against inadvertent actuation. The switching device is then reachable, and thus actuatable, exclusively via the peg.

Preferably, a covering element surrounding the switching device is provided when an opening region in the direction of the actuating element. The actuating element or actuating peg then actuates the switching device through the opening region. Thus, as in the embodiment described above, inadvertent actuation of the switching device when the branches are not brought together can be avoided, since only the specifically designed actuating element has access to the switching device. This increases the safety of the patient during the intervention, since unwanted current feed into the tissue being treated cannot occur.

In another embodiment, the switching device is configured as a switch, button or similar element. Thus the arrangement can be realised by simple means with conventional components.

In a preferred embodiment, the switching device is designed as a reed contact, which is arranged, for example, within the corresponding branch or gripping device. In order to actuate the reed contact, a magnet element is provided at the branch or the gripping device lying opposing the reed contact. Through the bending or folding of the relevant branch or by further movement of the at least one region of the gripping device after reaching the minimum spacing, the switch, that is the reed contact, and thereby the current feed can be activated without physical contact. This represents a particularly user-friendly embodiment, particularly since cleaning of the instrument can be carried out easily due to the switch being arranged in the interior of the instrument. The arrangement of the switch in the interior of the instrument also offers no seepage routes for liquids and other dirt on and in the instrument.

In particular, the objectives of the invention may be achieved with an electrosurgical instrument for coagulating and/or cutting biological tissue, including: a shaft, at least one first gripping device and one second gripping device at a proximal region of the instrument for its operation, wherein the gripping devices are movable toward one another, at least one electrode part at a distal region of the instrument for conducting a high-frequency current through the tissue, wherein the electrode part can be brought by means of the gripping devices from a rest position into a working position, current feed devices for feeding the high-frequency current from a high-frequency generator to the at least one electrode part, a switching device for activating the high-frequency current with the gripping devices brought together, and at least one elastically deformable element which is arranged on and/or in the instrument such that at least one region of the gripping devices can be moved further for actuating the switching device when the electrode part is in the working position.

The elastically deformable element and the switching device are configured and arranged in relation to one another such that the switching device can be actuated on further movement of the at least one region of the gripping devices. The region of the gripping devices also passes through different "travel regions," as explained above in similar manner. Passing through a first "travel region" (on moving the gripping devices toward one another) serves to move the at least one electrode part in order to bring it into the working position. As soon as the working position is reached, the corresponding region of the gripping devices can be further moved, due at least to the elastically deformable element, such that actuation of the switching device is made possible. The corresponding gripping device passes through a second "travel region" in order to enable actuation of the switching device to activate the HF current—via the gripping device itself or an additional component. The current feed devices are, in principle, constructed similarly in instruments of this type to the branch instruments described above. The switching device comprises part of the current feed devices and, according to the invention, can be actuated by the simplest means.

With this arrangement, complex hand or foot switches can be dispensed with so that the overall operation area remains less cluttered. In addition, the start of a coagulation process and/or a cutting process can be precisely determined in conjunction with the positioning of the electrodes on the tissue being treated.

Furthermore, in instruments of this type, deactivation of the current feed can be carried out as described above. The instruments described above ensure that the electrode remains in the working position and the jaw part remains in the closed position. For example, a latching mechanism may serve to maintain the working position or the user may have to apply active force to maintain the working position.

The activation of the high frequency current can be provided both for instruments for open surgery and for instruments for endoscopy, for example, laparoscopic instruments. Instruments for endoscopy, for example, laparoscopic instruments can also be designed as described above without difficulty, ensuring their easy and reliable use. Laparoscopic instruments have branches—just as, for example, bipolar scissors do—which can be actuated in scissor-like manner and via which the electrode parts are moved.

In a preferred embodiment, a support element, which is movable via the gripping devices, is arranged within the shaft for supporting the at least one electrode part and for moving the electrode part from the rest position into the working position. The support element is configured, for example, as a type of push rod and enables the positioning of the electrode part on the tissue being treated, via the gripping devices. The rest position of the electrode part is preferably to be understood as that position wherein the electrode part is placed within the shaft and is essentially inaccessible from outside. A movement of the support element in the extension direction of the shaft enables "moving out" of the electrode part from the shaft so that it can be positioned on the tissue being treated.

If an instrument has two electrodes which, for example, comprise a bipolar arrangement as a jaw part, these electrodes can also be transferred from a rest position into a working position by means of the support element. The rest position may be defined, for example, by the opened jaw part, whereas the working position is defined by the closed jaw part. In order to enable closing of the jaw part, the jaw part is moved in the extension direction of the shaft to the proximal end of the instrument, wherein the moving in of the electrode parts into the shaft brings about the closing of the jaw part.

Preferably, a spacing element (which becomes effective upon the bringing together of the gripping devices) is provided in or on the instrument such that it can determine the working position of the at least one electrode part. The first travel region of a gripping device is therefore also defined by the spacing element. For this purpose, the support element comprises, for example, at least one limit device as a spacing element, which, for example, projects from the support element and cooperates with at least one first shaft projection such that the working position of the electrode part can be determined by the cooperation. The limit device is arranged at the support element such that it is movable with the support element via the gripping devices. The shaft projection can be arranged, for example, within the shaft and can project therefrom into the interior of the shaft. Thus the shaft projection acts as a stop element as soon as the limit device has reached the shaft projection.

In a preferred embodiment, the elastically deformable element is arranged at the support element in such a manner. The support element comprises at least one second limit device which cooperates with at least one second shaft projection which comprises the switching device, such that the switching device can be actuated on further movement of the at least one region of the gripping devices in the extension direction of the shaft at least by deformation of the elastically deformable element by means of the second limit device. Preferably, the elastically deformable element is configured such that it is compressible. In this embodiment, the support element can comprise two sections which are connected to one another via the elastically deformable element. A distal section comprises the first limit device, which cooperates with the first shaft projection on "moving out" of the electrode part so that the working position of the electrode part is defined. A proximal section comprises the second limit device wherein further movement of the relevant gripping part causes further movement of the proximal section in that at least the elastically deformable element deforms. Preferably therefore, the proximal section moves in the direction of the distal section, wherein the second limit device actuates the switching device arranged at the second shaft projection. Further movement of the distal section is herein prevented by the first limit device, that is, the proximal section is movable even when the distal section is static. However, the elastically deformable element is to be configured such that, despite their coupling via the elastically deformable element, the two sections of the support element are displaceable when moving synchronously—while passing through the first travel region of the relevant gripping device—and thus a transition from the rest position of the electrode part to the working position is possible. The second travel region, through which the at least one region of the gripping devices is moved, can only be passed through if a sufficiently large force is exerted on the elastically deformable element to enable a deformation. This is ensured inter alia because the distal section of the support element already lies against the stop. Actuation of the switching device takes place via the proximal section although the distal section no longer moves; the proximal section pushes against the distal section. In order to ensure "moving in" of the electrode part into the shaft (that is, transfer of the electrode part from the working position into the rest position again), a restraining mechanism is provided which holds the two sections together during the moving in. This prevents overstretching of the elastically deformable element.

The first limit device described here, which cooperates with the first shaft projection, corresponds in principle to the spacing element described above. A type of spacing element, limit device or similar device is also advantageous in tubular shaft instruments of the type described here, in order to stipulate the two travel regions and thus to enable further movement of the at least one region of the gripping devices, even without further movement of the at least one electrode part.

The support element and the elastically deformable element are movable by means of a pushing element connected to the support element and running along the shaft, wherein the first gripping device is provided for holding the instrument and the second gripping device is provided for actuating the pushing element. Thus the pushing element transmits the movement of the respective gripping device to the support element in order to transfer the electrode part from the rest position into the working position and vice versa and, also, to enable actuation of the switching device. If the pushing element can be guided externally along the shaft, a mechanism is preferably provided which enables the user to move the support element by simple means. The pushing element preferably comprises a thumb element connected thereto as the second gripping device, so that the user can move the gripping device through both travel regions by a simple thumb movement. The user holds the instrument by means of the first gripping device, for example, a handle arranged on the shaft. It is also possible to move the pushing element by means of a branch element as the second gripping device, wherein the branch element is articulated at a first end at the handle of the shaft and is connected at a second end to the pushing element via a lever element (52*c*) articulated to said pushing element and to the branch element (52*b*). The movement of the pushing element is then carried out by the user as though operating a pair of scissors. Both movement mechanisms enable precise actuation of the support element as well as the switching device.

Preferably, the elastically deformable element is configured as a helical spring element. Given suitable design of the helical spring element, it is ensured that the two sections of the support element can be moved synchronously without difficulty if the electrode part is to be transferred from the rest position to the working position. Furthermore, the helical spring permits the further movement of the gripping device by simple means, to actuate the switching device. Other types of spring, for example leaf springs, can also be used.

In the case of shaft instruments of this type, further movement of the relevant gripping device can also be carried out via an elastically deformable element which, for example, comprises a predetermined bending or folding site. Thus the elastically deformable element can be arranged at at least one gripping device and interposed within it and configured such that a predetermined bending or folding site is provided at the gripping device by the elastically deformable element. Preferably, the elastically deformable element can also be provided as a gripping device section which is configured to be narrower than the surrounding gripping device regions, so that a predetermined bending or folding site is provided at the gripping device by the gripping device section. The predetermined bending or folding site permits bending or folding of the gripping device by simple means at the desired site without excessively loading the other regions, for example, by bending. A narrowed bending and folding region is typically formed integrally with the relevant gripping device, so that the instrument is simple to manufacture and can be easily cleaned after an intervention. The spacing element is then arranged such that the first travel region of the relevant gripping device is thereby defined, that is, on bringing together the gripping devices and reaching the spacing element, the working position of the electrode part is also reached. Thereafter, one of the gripping devices can only be further moved by actuating the switching device.

Different materials may be used for the gripping device (or the branch of the branch instrument described above) and elastically deformable element and/or different cross-sections, thus permitting the stipulation of a defined further movement of the at least one region of the gripping devices. The configuration of the elastically deformable element merely as a narrowed region which comprises branch or gripping device material, also allows a simple and easily operated embodiment of the subject matter of the invention.

The elastically deformable element can also be configured as a compressible element at the respective gripping device, so that actuation of the switching device is enabled by compression of the gripping device.

The switching device can be configured as a switch, button or similar element, as described in greater detail above. Commercially available components of this type permit simple manufacturing of the inventive instrument.

The switching device can preferably also be configured as a reed contact, wherein a magnet element is arranged at at least one gripping device or at the second limit device, for actuating the reed contact. Through the further movement of the gripping device and possibly also the limit device, the reed contact may be switched without physical contact. The advantages of this embodiment are found—as described above in greater detail—particularly in the manufacturing of the instrument. Thus, with a contactless switching possibility, complete covering of the switching device can be provided. This allows seepage routes for liquids and other dirt to be avoided.

As previously mentioned, the instrument according to the invention can be configured both for open surgery and for endoscopy, as well as for unipolar or bipolar technology.

Preferably, the elastically deformable element is made from a material which, apart from being elastic, has a high degree of wear resistance. For this purpose, for example, a polyetheretherketone (PEEK) or similar plastics can be considered. Polyetherketones (PEK) are high temperature-resistant and resistant to most organic and inorganic chemicals. The elastically deformable element can also be made from spring steel. Commercially available spring elements of this type enable simple and economic manufacturing of the instrument.

BRIEF DESCRIPTION OF THE DRAWINGS

In the following, the invention will now be described in greater detail by reference to exemplary embodiments, which are explained in greater detail with reference to the enclosed drawings FIG. 1 illustrates a side view of a preferred embodiment of an electrosurgical instrument according to the invention.

FIG. 2 illustrates a side view of a further preferred embodiment of the electrosurgical instrument according to the invention.

FIG. 13 illustrates a side view of a further preferred embodiment of the electrosurgical instrument according to the invention.

FIG. 14 illustrates a side view of a proximal region of the instrument with a switching device of a further preferred embodiment of the electrosurgical instrument according to the invention in a simplified representation.

FIG. 15 illustrates a distal end of a tubular shaft according to a preferred embodiment with the jaw part open.

FIG. 16 illustrates the distal ends of the tubular shaft of FIG. 15 with the jaw part closed.

DETAILED DESCRIPTION OF THE INVENTION

Figure 3:
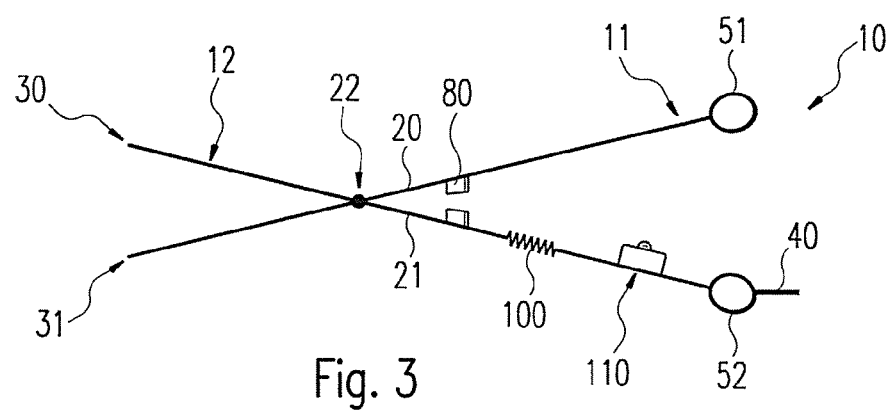
FIG. 3 illustrate a side view of a simplified representation of a further preferred embodiment of the electrosurgical instrument according to the invention.

In the description that follows, the same reference signs are used for the same parts and for parts which act similarly.

FIG. 1 shows a preferred embodiment of an electrosurgical instrument 10 according to the invention for open surgery, having an arrangement for activating high frequency current. The instrument is shown in a side view. The two branches 20, 21 of the electrosurgical instrument 10 are connected to one another via an articulated connection 22 and are moveable (for example, pivotable toward each other) about the articulated connection 22. The articulated connection 22 divides the instrument 10 or the branches 20, 21 in principle into a proximal region 11 and a distal region 12. In the proximal region 11, gripping devices 51, 52 for operating the instrument 10 are provided adjacent to the branches 20, 21. Arranged at the branches 20, 21 in the distal region 12 are mutually opposed electrode parts 30, 31, by means of which, for example, a vessel or tissue can be grasped and, by feeding in high frequency current, coagulated or possibly cut. The feeding in of the current takes place via a current connecting element or a current feed device 40 formed at one of the branches 21 for connecting the electrosurgical instrument 10 to an HF generator (not shown). The HF current is fed to the electrode parts 30, 31, for example, through electrical lines (not shown) running in the instrument 10.

A spacing element 80, which comprises two mutually opposed limit elements, is arranged in the proximal region 11 of the instrument 10. The limit elements are made integrally with the branches 20, 21, preferably from the same material. Due to the spacing element 80, a minimum spacing between the electrodes 30, 31 cannot be undershot, so that a short circuit between the electrode parts 30, 31 when the branches 20, 21 are brought together is avoided. The spacing element 80 also prevents a complete bringing together of the branches 20, 21, even in the proximal region 11.

One of the branches 21 comprises a switching device 110 (for example, a button 110*a*) as part of the current feed devices, which is arranged such that it could be actuated by contacting the opposing branch 20. Actuation activates the current feed (from the HF generator) so that the electrode parts 30, 31 can be used to treat tissue. Since the spacing element 80 now prevents further bringing together of the branches 20, 21 on reaching the minimum spacing between the electrode parts 30, 31, even in the proximal region 11, an elastically deformable element 100 is provided at the branch 20 opposing the switching device 110. The elastically deformable element 100 enables bending or folding of the branch 20 for actuating the button 110*a*, even with the branches 20, 21 brought together and the limit devices of the spacing element 80 brought together. The branches 20, 21 or the gripping devices 51, 52 can therefore be brought further together even after reaching the minimum spacing, that is, the branch 20 having the elastically deformable element 100 and the gripping device 51 can be further moved, or in this case, bent in the direction of the switching device 110.

Thus, on bringing together, the gripping device 51—together with the branches—moves through a first "travel region" until the minimum spacing is reached, defined by the spacing element 80. Since the spacing element 80 prevents a complete bringing together of the branches 20, 21, even in the proximal region 11, a second "travel region" of the gripping device 51 can only be passed through as a result of the elastically deformable element 100, wherein actuation of the switching device 110 is thereby enabled. The spacing element 80, the elastically deformable element 100 and the switching device 110 are to be configured and arranged in relation to one another such that the branch lying opposing the switching device 110 can be brought into contact with the switching device 110. Thus the switching device 110 can be actuated and the high frequency current for treating the tissue activated.

The elastically deformable element 100 is therefore arranged between the spacing element 80 and the switching device 110, wherein the spacing element 80 is provided in the proximal region 11 of the instrument 10. The elastically deformable element 100 is made, for example, from polyetheretherketone and is interposed within the branch 20. Thus the elastically deformable element 100 can form a predetermined bending or folding site so that defined bending or folding can be stipulated. The other branch regions are therefore not subjected to any bending loading.

FIG. 2 shows an electrosurgical instrument 10 according to a further preferred embodiment. The design of the instrument 10 substantially corresponds to that shown in FIG. 1. However, the spacing element 80 in FIG. 2 is arranged in the distal region 12 of the branches 20, 21. The elastically deformable element 100 also differs from that in FIG. 1. The elastically deformable element 100 in FIG. 2 is provided in this exemplary embodiment as a section that is narrower than the branch 20. This has the advantage that the elastically deformable element 100 can be formed integrally with the branch 20, preferably from the same material. The instrument 10 can thus be manufactured by simple means. In addition, the instrument 10 is easily cleaned after an intervention because no join edges or similar interruptions are provided at the branch 20 and the wear resistance of different materials does not have to be considered.

FIG. 3 shows a further preferred embodiment of the electrosurgical instrument according to the invention. The simplified illustration shows an instrument which essentially corresponds to that described in relation to FIG. 1. However, the elastically deformable element 100 is arranged at the branch 21 at which the switching device 110 is provided. Thus the switching device 110 can be brought to the opposing branch 20 for actuation in that the corresponding gripping device 52 is moved further.

Figure 4:
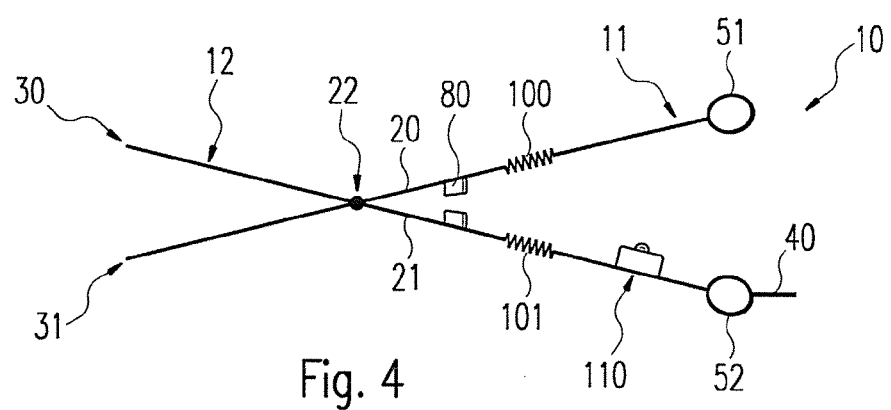
FIG. 4 illustrate a side view of a simplified representation of a further preferred embodiment of the electrosurgical instrument according to the invention.

The instrument shown in FIG. 4 according to a further preferred embodiment differs from that shown in FIG. 1 by having an additional elastically deformable element 101, so that an elastically deformable element is arranged at each of the branches 20, 21. Both branches 20, 21 and the gripping devices 51, 52 can be moved together, that is, bent or folded, to actuate the switching deice 110.

Figure 5:
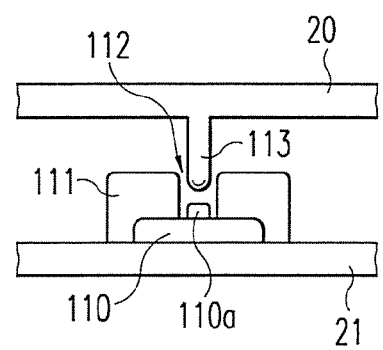
FIG. 5 illustrates a switching device with actuating possibility of a further preferred embodiment of the electrosurgical instrument according to the invention.
Figure 6:
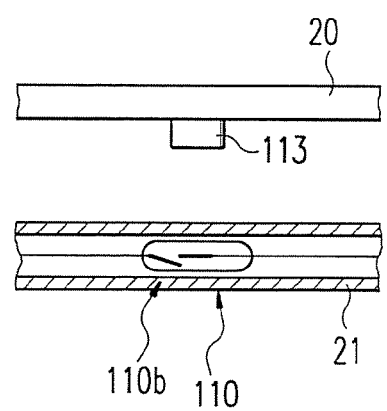
FIG. 6 illustrates a switching device with actuating possibility of a further preferred embodiment of the electrosurgical instrument according to the invention.

FIGS. 5 and 6 each show sections of an electrosurgical instrument 10 according to the invention, wherein regions of the branches 20, 21 with suitable switching devices 110 are shown. According to FIG. 5, the switching device 110 is configured as a button 110*a*. An actuating element 113 in the form of a peg, which is formed, for example, integrally with the branch 20 is arranged at the opposing branch 20. The actuating element 113 enables specific actuation of the button 110*a*. In contrast thereto, actuation of the switching device 110 in the embodiment according to FIGS. 1 to 4 takes place via the respective opposing branch itself; the switching device 110 and the opposing branch are brought into mutual contact by further movement of the corresponding gripping device(s). As shown in FIG. 5, the switching device 110 further comprises a covering element 111 surrounding it, with an opening region 112 formed in the direction towards the actuating element 113. The actuating element 113 actuates the switching device 110 through the opening region 112. The covering element 111—or shield—prevents accidental actuation of the switching device 110, since the button 110*a* is accessible only to the actuating element 113. This increases safety for the patient during an intervention, since no unintentional current feed to the treated tissue can occur.

FIG. 6 shows a reed contact 110*b* as the switching device 110 arranged in one of the branches 21, which can be actuated by a magnet element as the actuating element 113 arranged at the opposing branch 20. By means of further movement of the corresponding gripping device after reaching the minimum distance, the switch, that this the reed contact 110*b* and thus the current feed can be activated without physical contact. The reed contact 110*b* provided within the branch 21 enables easy cleaning of the instrument 10 following an intervention, since no seepage routes for liquids and other dirt are provided on or in the instrument 10 and, in particular, in the region of the switch. There are also no edges or similar areas of unevenness to make cleaning difficult.

In order to facilitate cleaning, however, covers made, for example, from plastics can be provided at the switching device 110 formed externally at the branch, so that seepage routes and, particularly, contamination of the switching device 110 itself are avoided.

Figure 7:
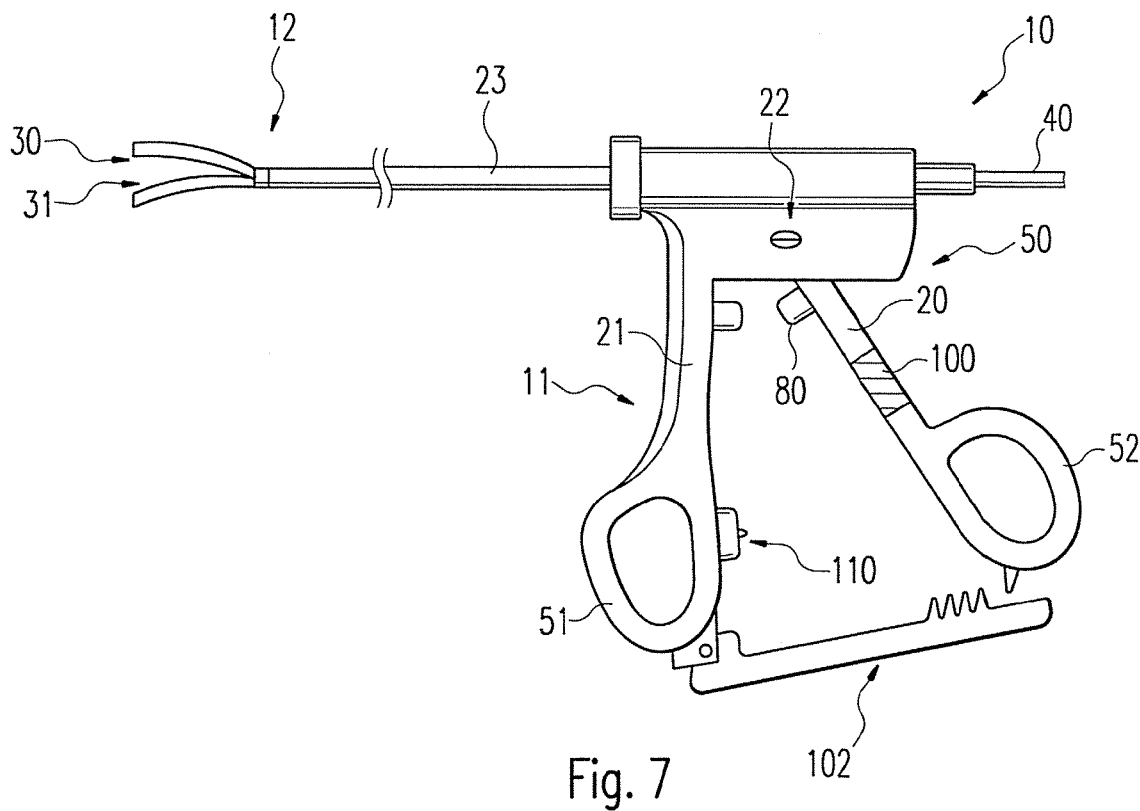
FIG. 7 illustrates a side view of a further preferred embodiment of the electrosurgical instrument according to the invention.
Figure 8:
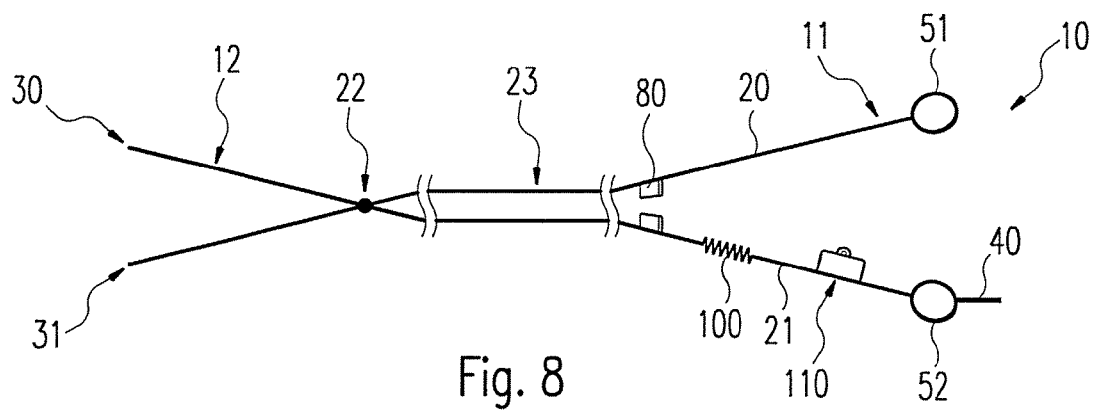
FIG. 8 illustrates a side view of a simplified representation of a further preferred embodiment of the electrosurgical instrument according to the invention.

FIGS. 7 and 8 show further embodiments of the instrument according to the invention, wherein the instruments shown are provided for endoscopy. FIG. 7 shows a laparoscopic instrument 10 with branches 20, 21, which can be actuated with a gripping element 50 at the proximal region 11—similarly to the instruments described above—in scissor-like manner. In practice, the branches 20, 21 are usually formed in the proximal region 11 such that only one branch 20 is movable, whilst the other branch 21 is formed, for example, integrally with the gripping element 50 and is therefore fixed. Pistol-form handles are often used here. Arranged at the distal region 12 of the instrument 10 are the electrode parts 30, 31 for grasping tissue and for passing high frequency current through the tissue. The branches 20, 21 are extended via a deflecting mechanism (not shown) constructed in a tubular shaft 23, so that the movement of the branches 20, 21 in the proximal region 11 can be transmitted to the electrode parts 30, 31. In order to actuate the branches 20, 21 and thereby the electrode parts 30, 31, the gripping devices 51, 52 are provided at the proximal region 11 of the branches 20, 21. The tubular shaft 23 is constructed between the proximal region 11 and the distal region 12 of the branches 20, 21 and permits the introduction of the electrode parts 30, 31 into a body cavity, wherein actuation of the electrode parts 30, 31 can be carried out from "outside" via the gripping devices 51, 52. The spacing element 80, the elastically deformable element 100 and the switching device 110 are arranged in this embodiment in the proximal region 11 of the branches, in principle at the gripping devices, so that actuation can be carried out as with a scissor-type instrument for open surgery. Reference is made in this regard to the description relating to FIG. 1. The current feed device 40 enables connection of the instrument to the electrosurgical device. A latching device 102—here, for example, a ratchet—enables the holding of the electrode parts 30, 31 in their working (closed) position if necessary, wherein overcoming the latching device 102, that is, a movement of the gripping device 52 continuing beyond the latching device permits actuation of the switching device 110. Fundamentally, the instruments can also be designed such that the working and rest positions can be maintained even without additional devices.

FIG. 8 shows a simplified representation of a laparoscopic instrument 10. The figure makes clear that the branches 20, 21 for actuating the electrode parts 30, 31 are extended via the mechanism (not shown) arranged in the interior of the instrument 10, so that minimally invasive interventions can be carried out. Activation of the high frequency current via the spacing element 80, the elastically deformable element 100 and the switching element 110 takes place on the same principle as described with regard to FIG. 1.

It should be mentioned that laparoscopic instruments can be configured with other combinations of switching device, spacing element and elastically deformable element. Thus, for example, the spacing element 80 can also be arranged in the distal region 12 of the instrument 10 and possibly even on or at the electrode surfaces. The spacing element, for example, could then simultaneously be provided as a cutting section for electrosurgical cutting. The minimum spacing of the electrodes, and thus the spacing between the branches in the proximal region can also be set such that, the movable branch or gripping device can only be moved toward the fixed branch as far as a defined separation. A further deflection of the branch or gripping device beyond the first travel region would then not be provided, so that in this case an actual spacing element especially arranged externally on the instrument could be dispensed with. The spacing element would then be implemented restricting the travel of the branch. Reference is also made to the descriptions relating to FIGS. 1 to 6.

Figure 9:
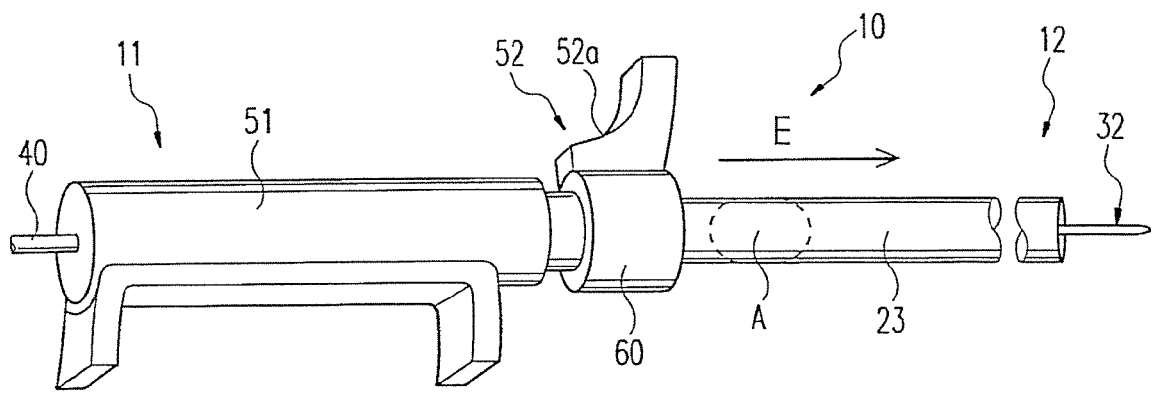
FIG. 9 illustrates a perspective view of a further preferred embodiment of the electrosurgical instrument according to the invention.

FIG. 9 shows a further embodiment of the instrument 10 according to the invention. The instrument is designed as a tubular shaft instrument, preferably for unipolar technology and can be used, for example, with a needle electrode 32. The instrument 10 comprises a shaft 23 at the distal end 12 of the instrument 10 and gripping devices 51, 52 arranged thereon at a proximal end 11. Arranged within the shaft 23 is a support element (not shown here) for supporting the electrode part 32 and for moving the electrode part 32 in the extension direction E of the shaft (i.e. linearly) from the rest position into the working position. A detailed view of the support element 70 is shown as detail view A in FIG. 10. In the rest position, the electrode part 32 is withdrawn into the shaft 23 and is thereby protected against external influences. For treating tissues, the electrode part 32 is "moved out" of the shaft 23 and so can be placed on the tissue. The movement of the support element 70 takes place via a pushing element 60 which is moveable along the shaft 23. A first gripping element 51 in the form of a handle is provided for holding the instrument 10, whilst a second gripping device 52 is connected to the pushing element 60 and is designed for placement of a finger, preferably a thumb. The pushing element 60 can therefore be displaced via the thumb element 52a, in order thus to move the support element 70. By this means, the electrode part 32 can be displaced extremely easily from the rest position to the working position, wherein the pushing element 60 with the thumb element 52a passes through a first travel region.

Figure 10:
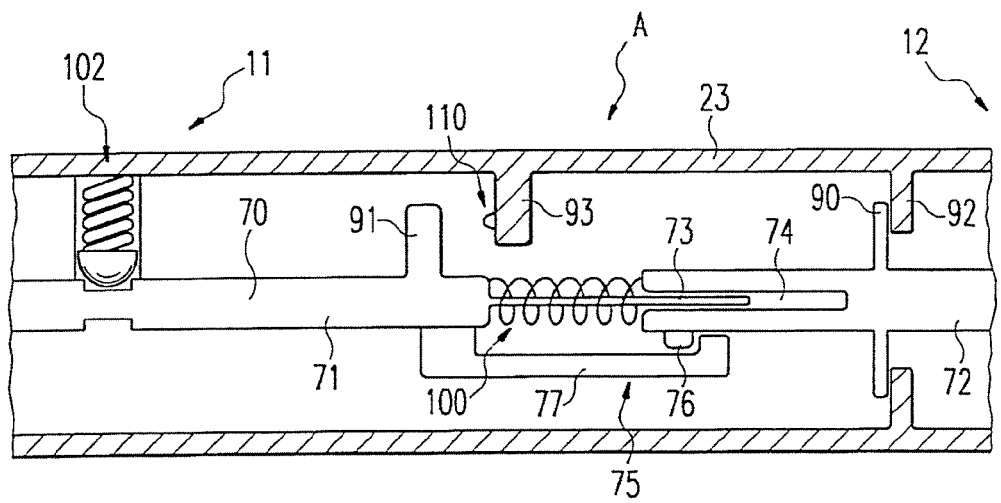
FIG. 10 illustrates a side view of an elastically deformable element of an electrosurgical instrument according to the invention, as can be used with the instruments of FIGS. 9, 11, 12 and 13.

The oval dashed line on the shaft 23 of the instrument 10 in FIG. 9 indicates that the mechanism just described for moving the support element 70 for actuating the switching device 110 as per FIG. 10 can be arranged there inside the shaft 23. FIG. 10 shows the corresponding detail view A.

The movement of the support element 70 via the pushing element 60 assumes a connection 60 of the support element 70 with the pushing element 60. The pushing element 60 could, for example, be connected to the support element 70 through slits in the shaft 23, and thereby ensure its movement.

FIG. 10 shows, in a detailed view A, a portion of the support element 70 in a side view, as it can be arranged in the shaft 23 described above, according to FIG. 9. The support element 70 is constructed from two sections as per FIG. 10, a distal section 72 and a proximal section 71. Arranged at the distal section 72 of the support element 70 is the electrode part 32 (not shown), in order to be moved with the support element 70 via the pushing element 60. The support element 70 comprises at its distal section 72 a first limit device 90, which projects from the support element 70 and cooperates with a first shaft projection 92 such that, through the cooperation, the working position of the electrode part 32 can be set. This means that, due to a movement of the support element 70 in the direction of the distal end 12 of the instrument 10, the first limit device 90 makes contact with the first shaft projection 92 and thus prevents further movement of the support element 70. The limit device 90 and the shaft projection 92 are arranged relative to one another such that contact takes place as soon as the electrode part 32 reaches its working position.

The support element 70 is constructed such that, by means of its movement, a switching device 110 can be actuated via the second gripping device 52. As FIG. 10 shows, the distal section 72 of the support element 70 and the proximal section 71 are linked to one another via an elastically deformable element 100, in this case a helical spring. In this embodiment, a rod element 73 is arranged at the proximal section 71 as an extension of the proximal section 71 and engages in an opposing recess 74 of the distal section 72. The rod element 73 carries the elastically deformable element 100 and together therewith forms the connection of the distal and proximal sections 72, 71. The recess 74 of the distal section 72 is configured such that the rod element 73 and thus the proximal section 71 can move further toward the distal section 72, even when the first limit device 90 at the distal section 72 is already in contact with the first shaft projection 92 and further movement of the distal section 72 is thereby prevented. Pushing of the rod element 73 into the recess 74 is only possible, however, once a sufficiently large force acts on the elastically deformable element 100, so that its deformation—for example, compression—permits further movement of the proximal section 71. In order to enable further movement of the proximal section 71 in the extension direction E, the user must only move the pushing element 60 further in the direction of the distal end 12 of the instrument 10, that is, continue the movement for transferring the electrode part 32 from the rest position into the working position, wherein the pushing element 60 passes with the thumb element 52a through a second travel region. The application of the force is achieved in that the first limit device 90 cooperates with the first shaft projection 92 and simultaneously the pushing element 60 is moved further beyond the second travel region. The elastically deformable element 100 serves to provide stiffness between the distal and proximal sections 72, 71 so that the movement of both sections during the transfer from the rest position of the electrode part 32 into the working position can take place synchronously until the first limit device 90 cooperates with the first shaft projection 92. The elastically deformable element 100 thus pushes the distal section 72 along in the direction of the distal end 12 of the instrument 10 if the support element 70 is moved by means of the pushing element 60.

The proximal section 71 comprises a second limit device 91 which cooperates with a second shaft projection 93, wherein the second limit device 91 and the second shaft projection 93 are arranged such that the cooperation takes place only once the first limit device 90 is in contact with the first shaft projection 92. In this exemplary embodiment, the second shaft projection 93 comprises the switching device 110, which can be actuated by the cooperation of the second limit device 91 with the second shaft projection 93. This means that, through the pushing in of the rod element 73 at the proximal section 71 of the support element 70 into the recess 74 of the distal section 72 and through the compression of the elastically deformable element 100, the switching device 110 can be actuated and the current feed activated.

In order to hold the electrode part 32 or the electrode parts 30, 31 of a jaw part in its working position, if required a latching device 102 (which has, in principle, the same effect as the latching device as per FIG. 7) can be provided. A detent knob coupled via a spring with the tubular shaft engages in an annular groove on the support element 70. The detent knob is guided in detent knob guides (the components of the latching device are not specified in greater detail). On a pushing movement of the support element 70 in the extension direction E of the shaft, the detent knob latches into the annular groove and fixes the electrode in its corresponding position. Overcoming the latching (increasing the force acting on the support element) enables actuation of the switching device 110 as described above. If the current supply is to be interrupted, the restoring force of the elastically deformable element 100 would again cause latching in of the latching device 102. The user would possibly have to apply force again in order to transfer the electrode part or the electrode parts into its or their final rest position. However, the elastically deformable element 100 can also be configured such that its restoring effect at least additionally facilitates the transfer into the rest position. The switching device 110 is preferably configured as a button 110a, wherein deactivation of the current feed can take place by "releasing," that is separating the second limit device 91 from the switching device 110. That means that the force applied by the user on the pushing element is reduced or even entirely released. If the elastically deformable element 100 is not configured such that it promotes transfer into the rest position, the electrode part or electrode parts remain in their working position. A further switching device may possibly be provided for deactivating the current feed or the instrument is configured such that renewed actuation of the switching device brings about deactivation.

Fundamentally, the mechanism described above can also be realised for actuating the switching device 110 without the rod element 73 with the elastically deformable element 100 simply arranged between the sections 72, 71 of the support element 70. Herein, the rod element 73 serves for stabilising the support element 70 between the two sections 72, 71 and ensures reliable operation of the device. Furthermore, the length of the recess 74 determines the degree to which the spring element is compressible.

The shaft projections 92, 93 can be arranged, for example, within the shaft 23, possibly integrally with said shaft, and project therefrom into the interior of the shaft 23. Thus, the projections 92, 93 act as stop elements as soon as the limit devices 90, 91 have reached the shaft projections 92, 93. At the same time, the second shaft projection 93 carries the switching device 110. The projections 92, 93 may be provided as single elements or as a plurality of elements which comprise the respective stop element. The projections 92, 93 can also be provided as complete peripheral elements, for example, disk elements and thus form a type of narrowing of the shaft 23. The same applies in principle for the limit devices 90, 91 arranged at the support element 70. A limit device can comprise a single element or a plurality of such elements.

In order to ensure "moving in" of the electrode part 32 into the shaft 23 (i.e. transfer of the electrode part 32 from the working position back into the rest position), a restraining device 75 is provided which holds the two sections 71, 72 of the support element 70 together during moving in. In the exemplary embodiment according to FIG. 10, a lever 77 arranged at the proximal section 71 of the support element 70 engages behind a projection 76 arranged at the distal section 72, so that the proximal section 71 carries the distal section 72 with it on moving in of the electrode part 32. Without the restraining device 75, the elastically deformable element 100, insofar as it is fastened to both sections 71, 72 would be stretched on returning the electrode part 32, so that the transfer of the electrode part 32 from the working position into the rest position would possibly take place in uncoordinated manner.

Figure 11:
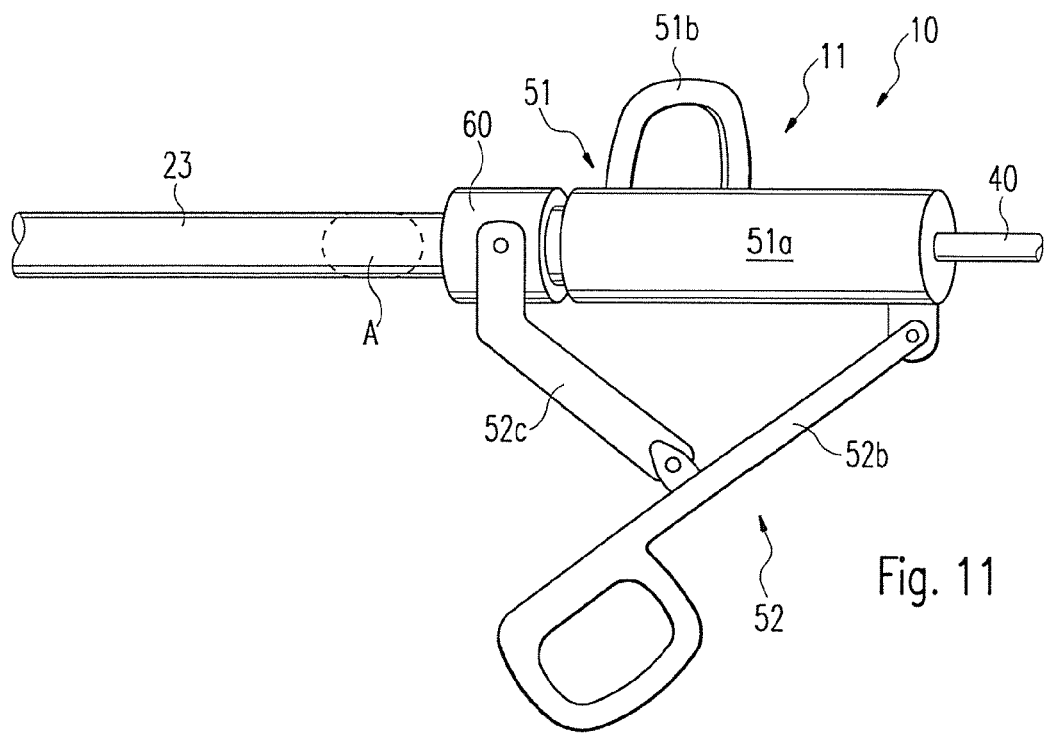
FIG. 11 illustrates a perspective view of a proximal region of a further preferred embodiment of the electrosurgical instrument according to the invention.

FIG. 11 shows a section of the electrosurgical instrument 10 according to the invention, specifically a proximal region 11 of the instrument 10 in a perspective view. Here also, a pushing element 60 for actuating the support element (not shown) is provided. The oval dashed line again signifies the detail view A as per FIG. 10 and indicates that the mechanism for moving the support element 70 for actuating the switching device 110 is provided within the shaft 23 as per FIG. 10. The pushing element 60 is movable here via a branch element 52b as the second gripping device 52, which is movably arranged, that is articulated, at a first end at the first gripping device 51, that is, the handle of the shaft 23, and connected at a second end to the pushing element 60 via a moveable lever element 52c. This means that the movable lever element 52c is articulated both to the pushing element 60 and to the branch element 52b. Furthermore, a loop 51b is mounted at the handle 51a in order to be able to move the branch element 52b similarly to a pair of scissors. As soon as the branch element 52b is moved in the direction of the shaft 32, the pushing element 60 can be moved along the shaft and therein actuates the support element 70 as described above. Moving through the first travel region of the branch element 52b, that is the second gripping device, the electrode part travels into the working position, whilst passing through the adjacent second travel region brings about actuation of the switching device 110 and activation of the current.

Figure 12:
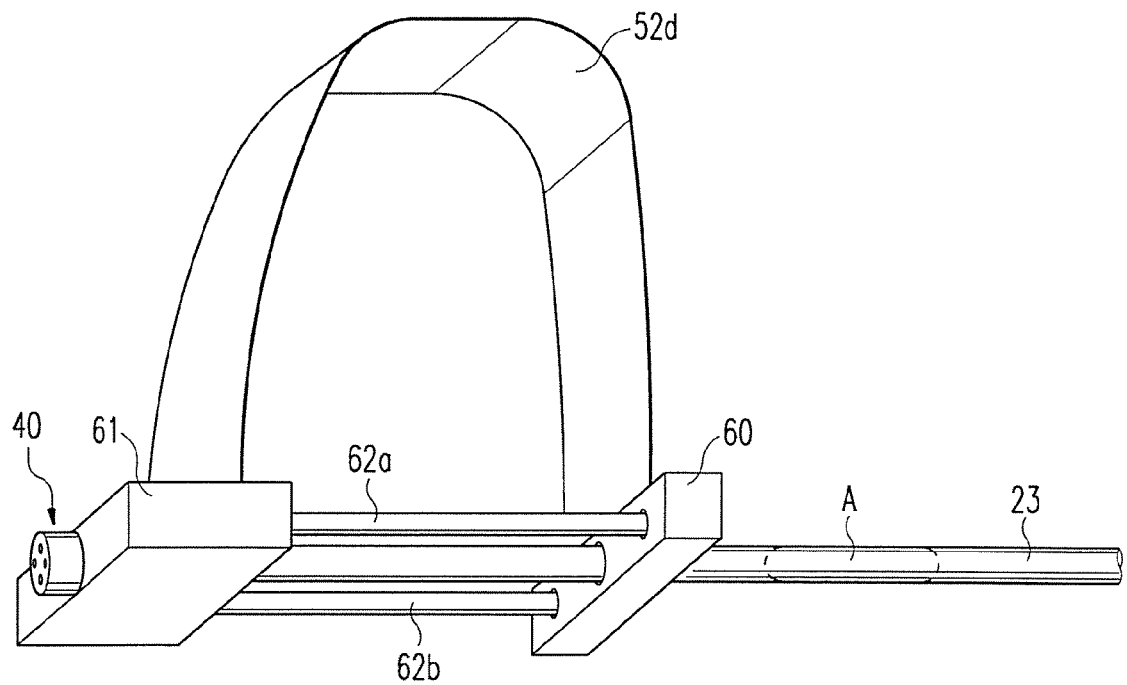
FIG. 12 illustrates a perspective view of a proximal region of a further preferred embodiment of the electrosurgical instrument according to the invention.

FIG. 12 shows a section of an electrosurgical instrument 10 according to an embodiment of the invention, specifically a proximal region 11 of the instrument 10 in a perspective view. Here, also, the oval dashed line indicates the detail view A as per FIG. 10, that is that within the shaft 23, the mechanism for moving the support element 70 for actuating the switching device 110 as per FIG. 10 is provided. The pushing element 60 is linked via an elastic element 52d (in principle, the handle) to a web 61 comprising the current feed device 40, so that the pushing element 60 can be moved toward the web 61 as soon as the elastic element 52d is pressed together. Guide elements 62a and 62b stabilise the pushing movement of the support element.

The handle according to FIG. 12 is particularly designed for actuating a bipolar arrangement. For example, a jaw part (not shown) comprising two electrode parts is opened (FIG. 15), whilst the pushing element 60 and the elastic element 52d are situated in a rest position. Through actuation of the handle, that is moving the pushing element 60 toward the web, the jaw part closes (FIG. 16), wherein the movement can also activate the switching device as described in relation to FIG. 11. As shown in FIG. 15, the jaw part is opened, that is the electrode parts 30, 31 are open (rest position). Actuation of the handle pulls the electrode parts 30, 31 back into the tubular shaft 23, wherein the jaw part closes, that is, the electrode parts 30, 31 move toward one another. The closing of the electrode parts 30, 31—as FIG. 16 shows—is supported by the two bowed regions 33a and 33b which are arranged immediately behind the electrode parts such that their contact with the interior of the tubular shaft causes the closing of the jaw part. The bowed regions 33a and 33b are typically formed by curving of the current feed devices. Since the working position is achieved by moving in of the electrodes, the arrangement according to FIG. 10 is preferably reversed here, that is, installed in the reverse direction, as provided, for example, in FIG. 9. Thus, by further advancing the pushing element 60 toward the web 61, the switching device can also be actuated according to the invention.

Preferably, the jaw part, i.e. the electrode parts, can remain closed to grasp the tissue only for as long as the force is, in principle, exerted via the gripping devices on the electrode parts. This is above all advantageous for rapid working. The elastic element 52d must be held in its compressed position in order for the electrode parts 30, 31 to remain closed. On "release," the jaw part opens and deactivation of the current feed takes place—on relevant positioning of the pushing element 60.

In the case of gripping devices without an elastic element (which should not be confused with the elastically deformable element) the electrode parts are possibly forced into their open position by a return mechanism, for example, a spring, provided that the force acting on the gripping devices is reduced. Furthermore, the latching device can fix the closed electrode parts. The same applies for the other embodiments and for unipolar arrangements. Active force application or a latching mechanism can enable maintenance of the working position and/or the current feed.

It is also possible to bring the electrode part or electrode parts (with both unipolar and bipolar arrangements) into their working position, wherein the latching enables maintenance of the working position. Despite the latching mechanism, it is still possible—as described above—to actuate the switching device. "Releasing" or force reduction via the gripping devices could then interrupt the current feed, although the working position would be maintained regardless. It is also possible to design the instrument such that, on deactivation of the current feed, the electrode part or electrode parts transfer into their rest position or into the open position. However, the instruments can be designed without any latching mechanism, so that the corresponding rest and working positions are reached by active actuation of the gripping devices.

FIG. 13 shows a further embodiment of an electrosurgical instrument 10 according to the invention. The oval dotted line here indicates again the detail view A as per FIG. 10, that is, that the mechanism for moving the support element 70 for actuating the switching device 110 is provided inside the shaft 23 as per FIG. 10. The movement of the gripping devices 51, 52 toward each other takes place similarly to the actuation of a syringe, wherein the ring-shaped second gripping device 52 is moved contrary to the first gripping device 51, in order to move the electrode part 32 into the working position and subsequently to activate the switching device 110. As the electrode 32, for example, a needle electrode 32 for unipolar coagulation and/or cutting could be used. The electrode is moved by means of the support element 70 in the interior of the tubular shaft 23. The progressive contrary movement of the gripping devices enables actuation of the switching device as described above.

The electrosurgical instrument 10 shown in FIG. 14 corresponds essentially to that shown in FIG. 13. The simplified representation shows a proximal region 11 of the instrument 10 in a side view, although here the switching device 110 is arranged outside the instrument 10 and can be actuated by bending or folding of, for example, the first gripping device 51 after the gripping devices have already been brought together. For this purpose, the elastically deformable element 100 is, for example, a bending element—as described in detail above (see, for example, FIG. 1)—arranged at the gripping device 51 in order, in the state with the gripping device 52 moved together, to move it further in the direction of the switching device 110. The switching device 110 can thereby be actuated. A spacing element 80 (stop) defines the first travel region for bringing together the gripping devices, whereas the elastically deformable element enables passing through of the second travel region.

With pistol-type handles, as are often provided with laparoscopic instruments, for example, a linearly movable gripping device can be moved toward the pistol grip to actuate the support element and therein move through the first travel region. A spring element coupled to the movable gripping device also allows the passing through of the second travel region in this embodiment for actuating the switching device. The spring element may be, for example, pre-tensionable It should be pointed out here that all the above described parts and in particular the details illustrated in the drawings are essential for the invention alone and in combination. Adaptations thereof are the common practice of persons skilled in the art.

The invention claimed is:

1. An electrosurgical instrument for at least one of coagulating and cutting biological tissue, comprising:
   two linked branches which can be moved toward one another, the two linked branches each having a respective longitudinal axis;
   gripping devices at a proximal region of each of the branches for bringing the branches together;

electrode parts at a distal region of each of the branches for grasping tissue and for conducting a high-frequency current through the tissue;

current feed devices for feeding the high-frequency current to the electrode parts from a high-frequency generator;

a switching device located at one of the branches or one of the gripping devices for activating the high-frequency current when the branches are brought together;

at least one spacing element to form a defined minimum spacing between the electrode parts, such that a short circuit between the electrode parts is prevented; and at least one elastically deformable element, which is arranged at one of the branches or one of the gripping devices such that, on closing the branches and reaching the defined minimum spacing, at least one region of the gripping devices can be moved further in the proximal region for actuating the switching device, wherein the elastically deformable element is interposed within at least one of the branches or gripping elements and is configured such that a predefined bending or folding site is provided by the elastically deformable element, wherein the elastically deformable element is arranged between the switching device and the at least one spacing element in the proximal region of the branches, wherein the at least one spacing element is arranged distal to the at least one elastically deformable element along the longitudinal axes and the at least one elastically deformable element is arranged distal to the switching device along the longitudinal axes.

2. The electrosurgical instrument according to claim 1, wherein the elastically deformable element is a section of at least one of the branches or one of the gripping devices, which is narrower than the surrounding portion of the branch or gripping device, thereby defining the predetermined bending or folding site.

3. The electrosurgical instrument according to claim 1, wherein the spacing element is configured as a limit element located on at least one of the branches.

4. The electrosurgical instrument according to claim 1, wherein the switching device and the branch or gripping device opposing the branch or gripping device on which the switching device is located are configured such that the switching device can be actuated by contact with the opposing branch or gripping device.

5. The electrosurgical instrument according to claim 1, further comprising an actuating element provided at the branch or gripping device opposing the branch or gripping device on which the switching device is located, the actuating element being arranged such that it actuates the switching device on further movement of the at least one region of the gripping devices when the branches have reached the defined minimum spacing.

6. The electrosurgical instrument according to claim 5, further comprising a covering element surrounding the switching device and having an opening region in the direction of the actuating element, wherein the actuating element actuates the switching device through the opening region.

7. The electrosurgical instrument according to claim 1, wherein the switching device is designed as a reed contact, and further comprising a magnet element provided at the branch or gripping device lying opposing the reed contact.

8. The electrosurgical instrument according to claim 1, wherein the switching device is one of a switch, a button, and a similar element.

9. The electrosurgical instrument according to claim 1, is configured for open surgery or for endoscopy.

10. The electrosurgical instrument according to claim 1, wherein the elastically deformable element is made from one of polyetheretherketone and spring steel.

* * * * *